(12) United States Patent
Baik

(10) Patent No.: US 6,322,520 B1
(45) Date of Patent: Nov. 27, 2001

(54) ALLERGY TESTING APPARATUS

(76) Inventor: Jennifer J. Baik, 3000 W. Olympic Blvd. #203, Los Angeles, CA (US) 90006

( * ) Notice: Subject to any disclaimer, the term of this patent is extended or adjusted under 35 U.S.C. 154(b) by 0 days.

(21) Appl. No.: 09/609,677

(22) Filed: Jul. 3, 2000

(51) Int. Cl.[7] .................................................. A61B 5/00
(52) U.S. Cl. ............................................................. 600/556
(58) Field of Search ................................. 600/556, 300; 604/47

(56) References Cited

U.S. PATENT DOCUMENTS 5,551,441 * 9/1996 Pitesky .................................. 600/556
5,673,705 * 10/1997 Pitesky .................................. 600/556

* cited by examiner

*Primary Examiner*—John P. Lacyk
*Assistant Examiner*—Brian Szmal
(74) *Attorney, Agent, or Firm*—George J. Netter

(57) ABSTRACT

Allergy testing apparatus (10) includes a housing (18) with opposed parallel sidewalls (22, 24) and a pair of pressure plates (30, 32) located therebetween. The surfaces between each sidewall and adjacent pressure plate are configured into shallow openings (28, 36), each set of complementary facing shallow openings forming a cylindrical opening (35). Threaded bolt (38) on being advanced secures picks (12) within individual openings (35). In use, the entire assembly of picks (12) is lifted by the gripping bar (26) and simultaneously pressed against the patient's skin.

8 Claims, 2 Drawing Sheets

ALLERGY TESTING APPARATUS

BACKGROUND

1. Background of the Invention

The present invention relates generally to human allergy testing apparatus, and, more particularly, to such apparatus enabling multiple simultaneous skin puncturing testing.

2. Description of Related Art

Diagnostic testing to determine which one or more substances a patient may have a particular sensitivity to, typically requires subcutaneously injecting a plurality of different biological agents at different test points on the patient. Subsequent examination of the various test sites will reveal to which substances, if any, the patient has a sensitivity or allergy.

A widely available device for making a test injection is an elongated needle-like member having several spaced apart points. In use, the pointed end is first dipped into a biological substance or extract, and then the pointed end punctures the skin to locate the test biological into necessary reactive relation to the patient. On a sensitivity reaction occurring at the test site, the allergenic substance is accordingly identified. Exemplary of such needle-like test devices are the picks disclosed in U.S. Pat. No. 5,193,794.

Since a patient may be sensitive to one or several different substances from among a large number of possibilities, identification of the particular allergens may require a large number of individual tests being made. To shorten testing time and reduce inconvenience to the patient, devices are available having a hand-held body with a plurality of integral needle-like structures extending from a common surface. In use, after loading the needle-like structures with test allergenic materials, all of the structures are pressed against a patient's skin simultaneously puncturing it to form a plurality of different tests. Such multiple test structures are relatively expensive and must be discarded after use. Representative of such devices are U.S. Pat. Nos. 3,289,670 (Krug); 2,522,309 (Simon); 3,556,080 (Hein); 4,871,452 (Baker); and 5,944,671 (White).

SUMMARY OF THE INVENTION

It is a primary object and aim of the present invention to provide a multiple allergen test apparatus which is relatively inexpensive to manufacture and simple to use.

Another object is the provision of such apparatus which can be repeatedly provided with unused picks and used picks can be removed for disposal.

Yet another object as in the previous objects is the provision of a hand-held housing which can be selectively assembled with a plurality of picks and disassembled at the conclusion of test use.

BRIEF DESCRIPTION OF THE DRAWINGS

These and other objects of the present invention will become more readily apparent upon reading the following detailed description and upon reference to the attached drawings in which.

DESCRIPTION OF A PREFERRED EMBODIMENT

Figure 1:
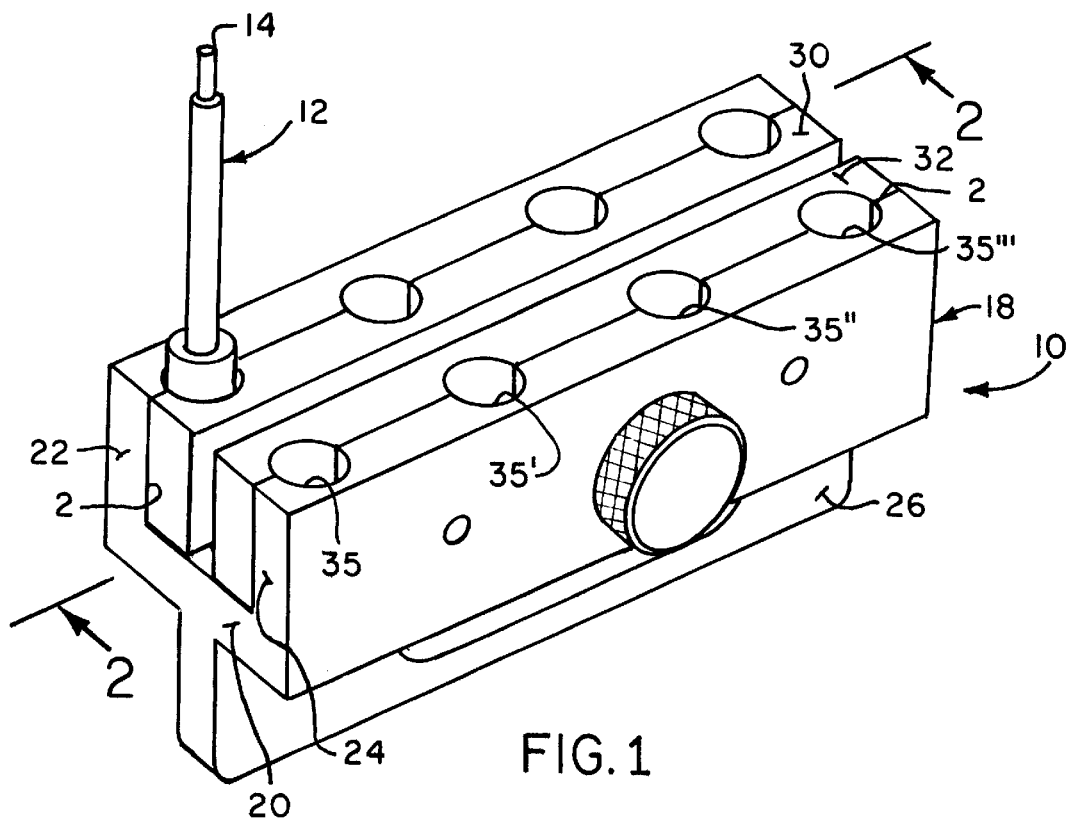
FIG. 1 is a perspective view of the allergy testing apparatus of this invention.

Turning now to the drawing and particularly FIG. 1, the allergy testing apparatus of the present invention is enumerated generally as 10 and is especially advantageous for performing simultaneous multiple allergy tests on a patient.

The basic device for puncturing the skin is a pick 12 (only one is shown) which is elongated and includes a puncture end portion 14 having several spaced apart points. The opposite mounting end portion 16 is cylindrical and is releasably mounted to the apparatus in a way to be described. Preferably, the picks 12 are constructed of a molded plastic and are identically shaped and dimensioned.

The cross-sectional dimensions of the picks puncture end portion 14 are relatively small so that the several points will induce biological test extract retention therebetween by capillary action.

The apparatus 10 further includes a housing with a base plate 20 and two identical sidewalls 22 and 24 extending upwardly from a common surface of the base plate in spaced apart parallel relation. A gripping bar 26 adapted for finger holding is integral with the base plate and centrally located between the sidewalls. Also, the bar 26 extends in a direction opposite to that of the sidewalls.

Figure 2:
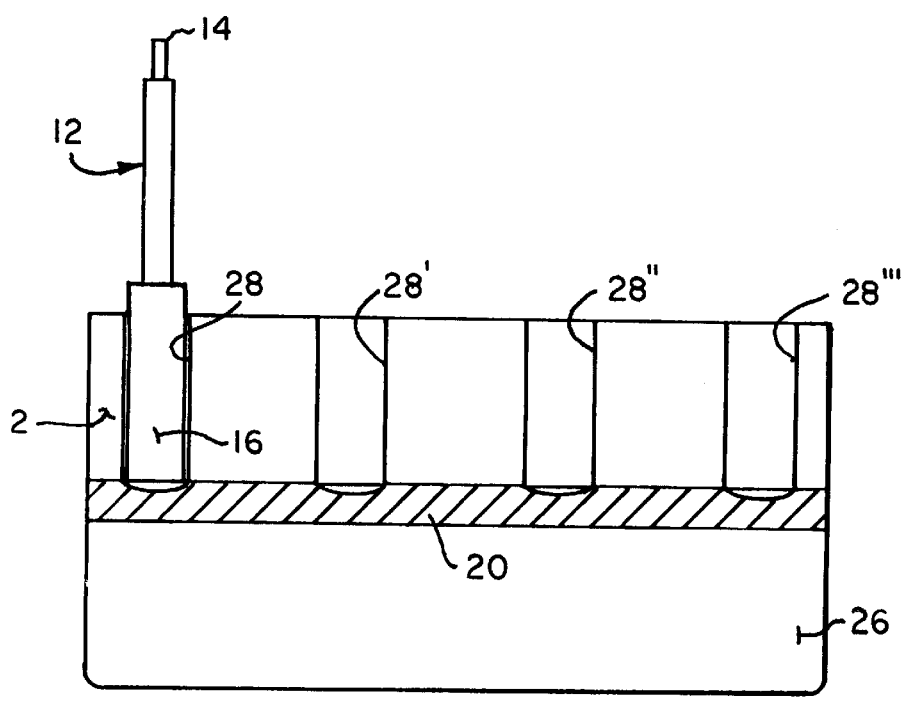
FIG. 2 is an elevational sectional view of an apparatus housing taken along line 2—2 of FIG.1.

As can be seen best in FIG. 2, the sidewall facing surfaces 25 and 27 each include a plurality of spaced shallow openings 28, 28', 28", 28"', the opening of each sidewall, respectively, being located directly opposite the complementary 35—opening in the other sidewall. In cross-section, the openings 28—are substantially semi-circular.

Figure 3:
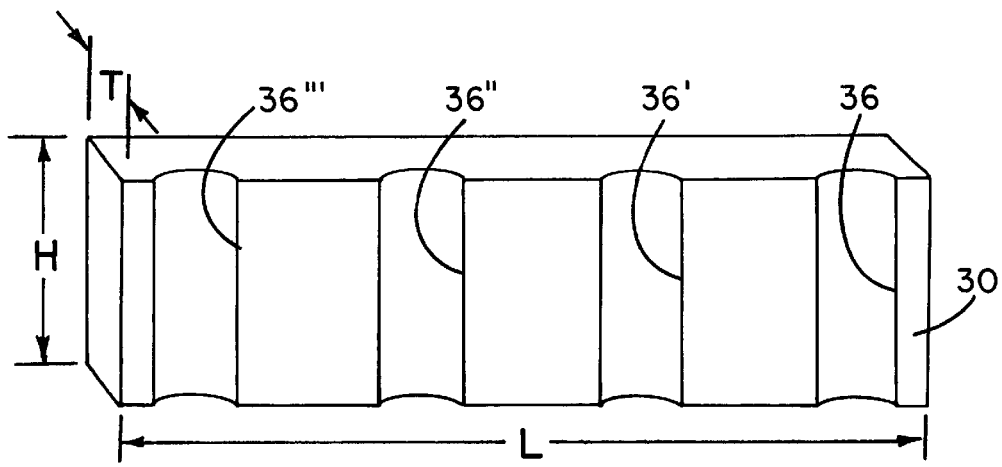
FIG. 3 is an elevational view of a pressure plate.

Turning simultaneously to FIGS. 1 and 3, two pressure plates 30 and 32 are shown which are fittingly and movably located within the space between the sidewalls 22 and 24 and when in the closed (retention) mode have a space 34 existing therebetween. Since the two pressure plates are identical, only pressure plate 30 will be described in detail. Specifically, the plate 30 is generally of parallelepiped geometry with a length (L) and height (H) corresponding to the facing sidewall.

The pressure plate thickness (T) is sufficient to enable forming a set of shallow openings 36, 36', 36", and 36"' identically shaped, sized and spaced corresponding to openings 28, - - - . Accordingly, when the pressure plate 30 is moved into contact with sidewall 22, the corresponding facing shallow openings form a set of cylindrical openings which, as will be shown, retain the individual picks 22 therewithin.

Figure 4A:
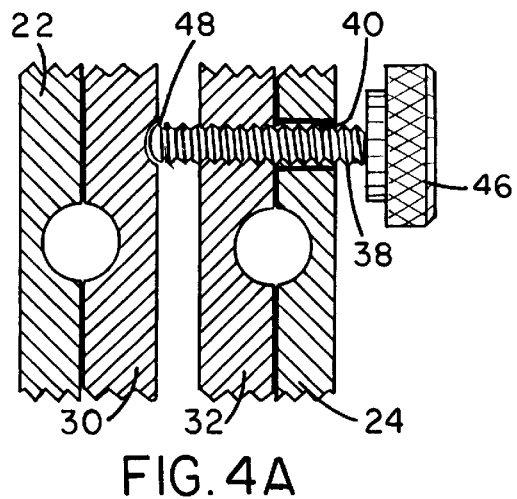
FIGS. 4A and 4B are plan, partially sectional and fragmentary views of the apparatus shown in pick-retaining mode and pick-released modes, respectively.
Figure 4B:
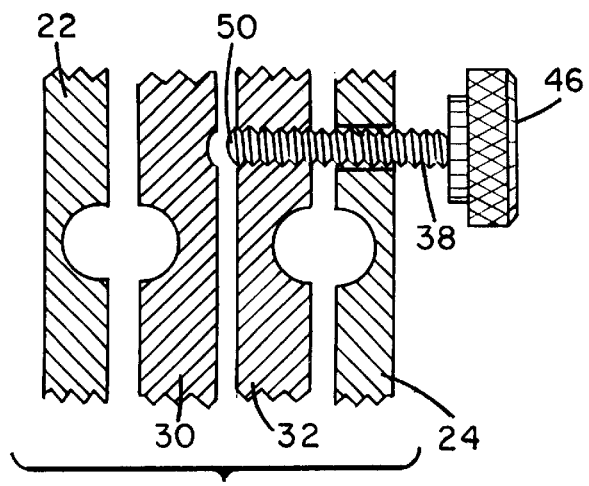

With reference now to FIGS. 4A and 4B, a threaded bolt 38 extends through an oversize opening 40 in sidewall 24 and threads within an opening 44 in pressure plate 32. The outer end of bolt 38 includes an adjustment knob 46, and the overall length of the bolt is such that the bolt inner end 48 can be brought into contact with the pressure plate 30 forcing it against the sidewall 22. More particularly, a shallow opening or declivity 50 is found in the pressure plate wall for receiving the bolt end 48 therewithin.

To use the apparatus 10, the bolt 38 is loosened to separate the pressure plates from the sidewalls, the required plurality of picks 12 are loaded into the sidewall/pressure plate openings, and the pressure plates are retightened to hold the picks in place. Biological extracts are placed on the pointed ends of the picks, and after grasping the gripping bar 26 with the fingers of one hand, the entire set of picks is forced against the skin of the patient for puncturing it and injecting the biological materials under the skin.

In accordance with the practice of the present invention, apparatus is provided for simultaneously achieving the testing for hypersensitivity of a human patient to a plurality of biological extracts which includes of the same plurality of picks removably mounted within a handheld housing. At the conclusion of test inoculation, the used picks are discarded and the housing may be used again.

Although the present invention is described in connection with a preferred embodiment, it is to be understood that those skilled in the appertaining art may contemplate changes that come within the spirit of the invention as described and within the scope of the appended claims.

What is claimed is:

1. Handheld apparatus for simultaneous puncturing of human skin at a plurality of different points for testing the hypersensitivity to the same plurality of different biological extracts, comprising:

a base plate with first and second sidewalls integrally related thereto, said sidewalls being parallel to each other and extending from a common surface of the base plate;

first and second pressure plates located between the said sidewalls and movable with respect to each other; a certain number of identical needlelike means less than the given plurality located between the first sidewall and the first pressure plate and the remainder of the given plurality of needlelike means located between the second sidewall and second pressure plate; and means for simultaneously moving the first pressure plate toward the first sidewall and the second pressure plate toward the second sidewall to grip the needlelike means therebetween.

2. Handheld apparatus as in claim 1, in which the second sidewall includes an oversize unthreaded opening extending therethrough; the second pressure plate includes a threaded opening aligned with the unthreaded opening in the second sidewall; and the means for moving includes a threaded bolt which extends through the unthreaded opening in the second sidewall and threads within the second pressure plate opening, said bolt having an inner end contacting the first pressure plate.

3. Apparatus in claim 2, in which the first and second sidewalls include surfaces facing one another leaving the same plurality of shallow openings; the first and second surfaces of pressure plates have the same plurality of shallow openings formed therein so as to respectively coact with the shallow openings of the sidewalls to form the same plurality of openings for grippingly receiving the needle-like means therewithin and allowing the needle-like means to extend outwardly in a common direction.

4. Apparatus as in claim 1, in which a gripping bar is integral with the base plate and extends outwardly away from said base plate.

5. Apparatus as in claim 1, in which the baseplate, sidewalls, and gripping bar are made of metal and the needle-like means are constructed of plastic.

6. Apparatus as in claim 2, in which the bolt has an adjustment knob connected to an outer end.

7. Apparatus as in claim 2, in which the first pressure plate includes a still further shallow opening positioned to receive the bolt inner end.

8. Apparatus as in claim 3, in which each of the shallow has a semicylindrical cross-section.

* * * * *